United States Patent [19]

Bove

[11] Patent Number: 4,988,825

[45] Date of Patent: Jan. 29, 1991

[54] OXIDATION OF ALDEHYDES AND KETONES USING ALKALI METAL PERBORATES

[75] Inventor: John L. Bove, Ridgewood, N.J.

[73] Assignee: Cooper Union Research Foundation, Inc., New York, N.Y.

[21] Appl. No.: 910,615

[22] Filed: Sep. 23, 1986

[51] Int. Cl.$^5$ .................. C07D 313/18; C07D 313/04
[52] U.S. Cl. .................... 549/272; 549/273; 549/295; 560/231; 562/528
[58] Field of Search ............... 549/272, 273, 295; 562/528; 560/231

[56] References Cited

U.S. PATENT DOCUMENTS

| | | |
|---|---|---|
| 3,122,586 | 2/1964 | Berndt et al. . |
| 3,154,586 | 10/1964 | Bander et al. . |
| 3,483,222 | 12/1969 | Sennewald et al. . |
| 3,716,563 | 2/1973 | Brunie et al. ............... 549/524 |
| 3,833,613 | 9/1974 | Field ............................ 549/272 |
| 4,160,769 | 7/1979 | Higley . |
| 4,213,906 | 7/1980 | Mares et al. ............... 549/272 |
| 4,286,068 | 8/1981 | Mares et al. ............... 549/272 |
| 4,338,260 | 7/1982 | Schirmann ............... 260/502 R |

FOREIGN PATENT DOCUMENTS 1096967 12/1967 United Kingdom ............... 549/272

OTHER PUBLICATIONS

Y. Ogata et al., Bulletin of the Chemical Society of Japan, vol. 52(2), (1979), pp. 635–636.
A. Baeyer et al., Ber., 1899, 32, 3625–3633.
A. Baeyer et al., Ber., 1900, 33, 858–864.
Ogata et al., Chem. Abst. 90:167685, (1979).
McKillop et al., Tetrahedron Letters, 24, No. 14, (1983), 1505–1508.
McKillop et al., *Tetrahedron*, 43, pp. 1753–1758 (1987).
A. Rashid et al., J. Chem. Soc. (C) (1967), pp. 1323–1325.

*Primary Examiner*—Glennon H. Hollrah
*Assistant Examiner*—Amelia A. Owens
*Attorney, Agent, or Firm*—Jacobs & Jacobs

[57] ABSTRACT

Aldehydes and ketones, other than acetone, are oxidized with an alkali metal perborate in the presence of an acid.

13 Claims, No Drawings

OXIDATION OF ALDEHYDES AND KETONES USING ALKALI METAL PERBORATES

The present invention is directed to the oxidation of aldehydes and ketones to the corresponding acids and esters, respectively using an alkali metal perborate as the oxidant.

The oxidation of ketones, including cyclic ketones, to esters through the use of peracids is known as the Baeyer-Villager Reaction (A. Von Baeyer and V. Villager, Ber., 1899, 32, 3265; 1900, 33, 858) While widely applied, particularly for the oxidation of cyclohexanone to epsilon-caprolactone, nevertheless the use of a peracid presents problems of safety and disposal and/or recycling of organic compounds.

The present invention provides a safe and economical process for oxidizing aldehydes and ketones using an alkali metal perborate, such as sodium perborate, as the oxidant. Alkali metal perborates are safe and economical to use, and the sodium borate by-product thus formed is safely handled and is a valuable product that can be sold in its own right. In addition, the oxidation is carried out under easily maintained reaction conditions and provides selectivities approaching 100% so that all of the starting aldehydes or ketones can be converted to final product by appropriate recycling. It can be seen that the use of the alkali metal perborate provides a substantial advance in the oxidation of aldehydes and ketones.

In particular, the present invention provides a method of preparing acids or esters, which comprises oxidizing an aldehyde (other than acetone) or a ketone with an alkali metal perborate in the presence of an acid.

With the exception of acetone, the present invention is applicable to the oxidation of aldehydes and ketones to form the corresponding esters and/or acids. Aromatic and aliphatic aldehydes and ketones may be used, such as benzaldehyde and methylethyl ketone and the like, as well as cyclic ketones, such as cyclohexanone and the like. Aliphatic and cycloaliphatic aldehydes and ketones containing olefinic unsaturation may likewise be employed to form the corresponding unsaturated ester and/or acid. When ketones are oxidized according to the present invention, the product obtained will be the corresponding ester, but in some cases a mixture of the ester and acid will be produced.

In a preferred embodiment, the present invention may be used for the preparation of esters and/or acids of the formula (I)

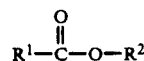  (I)

which comprises reacting an aldehyde or ketone of the formula (II)

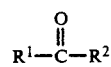  (II)

wherein $R^1$ is alkyl or aryl, $R^2$ is hydrogen, alkyl or aryl, or $R^1$ and $R^2$ are both hydrogen, or $R^1$ and $R^2$ together represent alkylene, provided that $R^1$ and $R^2$ may not both be methyl. When $R^1$ and $R^2$ is alkyl, $R^1$ and $R^2$ may be straight or branched chain alkyl, suitably straight or branched chain alkyl of from 1 to about 15 carbon atoms, such as from 1 to about 10 carbon atoms. When $R^1$ or $R^2$ is aryl, $R^1$ and $R^2$ may be aryl of from 1 to about 4 rings, including fused rings, and may suitably contain from about 6 to about 30 carbon atoms. Suitably, $R^1$ or $R^2$ maybe phenyl, naphthyl, biphenyl and the like. When $R^1$ and $R^2$ together represent alkylene, the alkylene may suitably be straight or branched chain alkylene of from about 1 to about 15 carbon atoms in the carbon-to-carbon chain, such as from 1 to about 10 carbon atoms in the carbon-to-carbon chain. Usually when $R^1$ and $R^2$ together represent alkylene, there will be from about 1 to about 30 carbon atoms in total, preferably from about 3 to about 15 carbon atoms in total.

In the above formulas (I) and (II), alkyl and alkylene may be unsubstituted or substituted by aryl, halogen, nitro or the like, while the aryl may be substituted by alkyl, preferably lower alkyl, i.e. from about 1 to about 6 carbon atoms, halogen, nitro or the like.

Preferably, $R^1$ may represent alkyl of from about 1 to about 10 carbon atoms, phenyl, or alkylene of from about 3 to about 15 carbon atoms with from about 3 to about 9 carbon atoms in the carbon-to-carbon chain, said alkyl, phenyl or alkylene being unsubstituted or substituted by halogen, cyano or nitro or, in the case of phenyl, lower alkyl. Further, $R^2$, or both $R^1$ and $R^2$ may represent hydrogen.

While sodium perborate tetrahydrate will normally be used, both in terms of economy and convenience, other alkali metal perborates may be employed of the formula (III)

$$MBO_3 \cdot nH_2O \quad \text{(III)}$$

wherein M is an alkali metal, preferably sodium or potassium, and n is 1 to 4, usually 4. Suitably, the oxidation is carried out with the perborate (III) in the presence of an acid that hydrolyzes in water to form hydronium ions, such as mineral acids, sulfonic acids, organic acids, and the like, but a Lowry-Bronsted acid or Lewis acid may also be used, such as $BF_3$. Glacial acetic acid is safe and economical and hence is presently preferred. Other useful organic acids include trifluoroacetic acid and formic acid.

When an organic acid is employed, it may also serve as a solvent. If a solvent or co-solvent is required, any suitable inert solvent may be employed, such as acetone, halogenated hydrocarbons, such as methylene chloride, chloroform and the like, aliphatic and aromatic esters, benzene and the like. It is noted that acetone, while a ketone, is nevertheless not oxidized by the perborate (III) and hence may be used as a solvent, if desired.

Usually, the oxidation will be initiated at a temperature of from about 30° to about 70° C., usually from about 40 to about 60° C. While lower temperatures can be used, reaction rates will necessarily be slower. Temperatures higher than about 70° C. may be used, if required or desired, depending upon the desired reaction rate. However, the reaction is exothermic and hence external cooling may be needed to control the reaction temperature, even at the lower temperatures employed.

The present invention is illustrated in terms of its preferred embodiments in the following Examples. In this specification and the appended claims, all parts and percentages are by weight, unless otherwise stated.

EXAMPLE 1

Preparation Of Epsilon-Caprolactone

To a 200 ml roundbottom flask was added 4.9 grams (0.05 mole) of cyclohexanone, 50ml of glacial acetic acid, and 11.4 grams (0.075 mole) of sodium perborate tetrahydrate. The mixture was heated to 50° C. using a water bath. The reaction temperature was maintained in the range of 50-55° C., while stirring the mixture with a magnetic stirrer for four hours, after which the reaction mixture was cooled to room temperature, and the solid sodium borate was separated from the mixture using section filtration. The acetic acid was stripped from the remaining liquid residue using a rotary evaporator, and the remaining epsilon-caprolactone was purified by vacuum distillation. Yield: 91% theoretical.

EXAMPLE 2

Preparation of Benzoic Acid

The procedure of Example 1 was followed using 5.3 grams (0.05 mole) of benzaldehyde as the starting material. Crude benzoic acid formed was purified by recrystallization. Yield: about 50% theoretical.

EXAMPLES 3-6

Following the procedure of Example 1, the ketones set forth below were oxidized with sodium perborate at a temperature of about 55° C. to provide the esters and acid set forth in Table 1 below.

TABLE 1

| Example | Starting Material | End Product | Yield |
|---|---|---|---|
| 3 | $CH_3C(O)C(CH_3)_2CH_3$ | $CH_3C(O)OC(CH_3)_2CH_3$ | 75% |
| 4 | cyclo-$(CH_2)_3$—C(O) | $(CH_2)_3$—C(O)—O (lactone) | 74% |
| 5 | cyclo-$(CH_2)_4$—C(O) | $(CH_2)_4$—C(O)—O (lactone) | 68% |
| 6 | cyclo-$(CH_2)_6$—C(O) | $(CH_2)_6$—C(O)—O (lactone) | 24% |
| | | $HOOC-(CH_2)_5-COOH$ | 38% |

I claim:

1. A method of preparing acids and esters of the formula (I)

which comprises oxidizing a compound of formula II

with an alkali metal perborate in the presence of an acid, wherein $R^1$ is alkyl or aryl, $R^2$ is hydrogen, alkyl or aryl, or $R^1$ and $R^2$ are both hydrogen, or $R^1$ and $R^2$ together represent alkylene, provided that $R^1$ and $R^2$ may not both be methyl, 2. A method according to claim 1, wherein the acid is a carboxylic acid.

3. The method according to claim 1, wherein the acid is acetic acid.

4. The method according to claim 1, wherein the compound of formula (II) is oxidized with sodium perborate in the presence of an acid.

5. The method according to claim 1, wherein $R^1$ and $R^2$ together represent straight or branched chain alkylene having from about 3 to about 9 carbon atoms in the carbon-to-carbon chain.

6. The method according to claim 1, wherein $R^1$ is alkyl or phenyl, and $R^2$ is hydrogen, alkyl or phenyl.

7. The method according to claim 6, wherein said alkyl is straight or branched chain alkyl of from about 1 to about 8 carbon atoms.

8. The method according to claim 1, wherein said alkali metal perborate is sodium or potassium perborate.

9. The method according to claim 1, wherein cyclohexanone is oxidized to epsilon-caprolactone with sodium perborate in the presence of acetic acid.

10. The method according to claim 2, wherein $R^1$ and $R^2$ together represent straight or branched chain alkylene having from about 3 to about 9 carbon atoms in the carbon-to-carbon chain.

11. The method according to claim 3, wherein $R^1$ and $R^2$ together represent straight or branched chain alkylene having from about 3 to about 9 carbon atoms in the carbon-to-carbon chain.

12. The method according to claim 4, wherein $R^1$ and $R^2$ together represent straight or branched chain alkylene having from about 3 to about 9 carbon atoms in the carbon-to-carbon chain.

13. The method according to claim 8, wherein $R^1$ and $R^2$ together represent straight or branched chain alkylene having from about 3 to about 9 carbon atoms in the carbon-to-carbon chain.

* * * * *